(12) United States Patent
Weisshaupt et al.

(10) Patent No.: US 9,468,359 B2
(45) Date of Patent: Oct. 18, 2016

(54) CONTROL APPARATUS

(71) Applicant: Aesculap AG, Tuttlingen (DE)

(72) Inventors: Dieter Weisshaupt, Immendingen (DE); Susanne Breitling, Buchen (DE); Theodor Lutze, Balgheim (DE)

(73) Assignee: Aesculap AG, Tuttlingen (DE)

( * ) Notice: Subject to any disclaimer, the term of this patent is extended or adjusted under 35 U.S.C. 154(b) by 489 days.

(21) Appl. No.: 14/026,498

(22) Filed: Sep. 13, 2013

(65) Prior Publication Data

US 2014/0052061 A1    Feb. 20, 2014

Related U.S. Application Data

(63) Continuation of application No. PCT/EP2012/055114, filed on Mar. 22, 2012.

(30) Foreign Application Priority Data

Apr. 12, 2011   (DE) .................. 10 2011 001 973

(51) Int. Cl.
| | |
|---|---|
| *A61B 1/00* | (2006.01) |
| *A61B 1/005* | (2006.01) |
| *G02B 23/24* | (2006.01) |
| *A61B 17/29* | (2006.01) |
| *A61B 17/00* | (2006.01) |

(52) U.S. Cl.
CPC ......... *A61B 1/00149* (2013.01); *A61B 1/0055* (2013.01); *A61B 1/00071* (2013.01); *A61B 17/29* (2013.01); *G02B 23/2476* (2013.01); *A61B 2017/003* (2013.01); *A61B 2017/00305* (2013.01); *A61B 2017/00314* (2013.01); *A61B 2017/291* (2013.01); *A61B 2017/2905* (2013.01)

(58) Field of Classification Search
CPC .......... A61B 17/22031; A61B 17/221; A61B 2017/22035; Y10S 227/902
See application file for complete search history.

(56) References Cited

U.S. PATENT DOCUMENTS

| | | |
|---|---|---|
| 338,310 A | 3/1886 | Smith |
| 2,515,365 A | 7/1950 | Zublin |
| 2,694,549 A | 11/1954 | James |

(Continued)

FOREIGN PATENT DOCUMENTS

| | | |
|---|---|---|
| CH | 119033 | 4/1927 |
| DE | 40 02 449 | 8/1990 |

(Continued)

*Primary Examiner* — David M Fenstermacher
(74) *Attorney, Agent, or Firm* — Lipsitz & McAllister, LLC

(57) ABSTRACT

A control apparatus for use in endoscopes or the like is provided which allows a user to work without fatigue. The control apparatus includes a proximal and distal end sections, each of which has an articulation zone, and a central section arranged therebetween, an outer hollow-cylindrical shaft, an inner cylindrical shaft, and a control element arranged between the shafts and having two or more force-transmitting longitudinal elements extending substantially from the proximal to the distal end section for coupling movement of the distal end section with movement of the proximal articulation section. The longitudinal elements are arranged in spaced-apart relation to one another at substantially regular angular distances which, as measured in a circumferential direction, are selected such that the longitudinal elements are guided without contact in a circumferential direction and optionally guided in contact with the outer and/or the inner shaft in a radial direction.

25 Claims, 13 Drawing Sheets

(56) References Cited

U.S. PATENT DOCUMENTS

| | | | |
|---|---|---|---|
| 2,712,436 | A | 7/1955 | McCune et al. |
| 2,739,089 | A | 3/1956 | Hageltorn |
| 3,096,962 | A | 7/1963 | Meijs |
| 3,190,286 | A | 6/1965 | Stokes |
| 3,625,200 | A | 12/1971 | Muller |
| 3,674,014 | A | 7/1972 | Tillander |
| 4,328,839 | A | 5/1982 | Lyons et al. |
| 4,600,037 | A | 7/1986 | Hatten |
| 4,706,659 | A | 11/1987 | Matthews et al. |
| 4,790,294 | A | 12/1988 | Allred, III et al. |
| 4,955,384 | A | 9/1990 | Taylor et al. |
| 5,152,744 | A | 10/1992 | Krause et al. |
| 5,179,934 | A | 1/1993 | Nagayoshi et al. |
| 5,437,630 | A | 8/1995 | Daniel et al. |
| 5,695,513 | A | 12/1997 | Johnson et al. |
| 5,741,429 | A | 4/1998 | Donadio, III et al. |
| 5,755,731 | A | 5/1998 | Grinberg |
| 5,807,241 | A | 9/1998 | Heimberger |
| 5,833,692 | A | 11/1998 | Cesarini et al. |
| 5,921,956 | A | 7/1999 | Grinberg et al. |
| 6,053,922 | A | 4/2000 | Krause et al. |
| 6,132,448 | A | 10/2000 | Perez et al. |
| 6,352,531 | B1 | 3/2002 | O'Connor et al. |
| 6,409,728 | B1 | 6/2002 | Ehr et al. |
| 6,447,518 | B1 | 9/2002 | Krause et al. |
| 6,817,974 | B2 | 11/2004 | Cooper et al. |
| 6,921,397 | B2 | 7/2005 | Corcoran et al. |
| 7,090,683 | B2 | 8/2006 | Brock et al. |
| 7,105,003 | B2 | 9/2006 | Hiltebrandt |
| 7,608,083 | B2 | 10/2009 | Lee et al. |
| 8,007,434 | B2 * | 8/2011 | Olson ............... A61B 1/00071 600/139 |
| 8,398,587 | B2 | 3/2013 | Dewaele et al. |
| 8,496,574 | B2 * | 7/2013 | Trusty ............... A61B 1/00105 396/17 |
| 8,728,116 | B1 * | 5/2014 | Janardhan ............. A61F 2/01 606/200 |
| 8,740,884 | B2 * | 6/2014 | Verbeek ............. A61B 1/0055 606/1 |
| 9,005,198 | B2 * | 4/2015 | Long ............... A61B 18/1477 606/41 |
| 9,039,676 | B2 * | 5/2015 | Klima ............. A61M 25/0138 604/528 |
| 9,055,941 | B2 * | 6/2015 | Schmid ........... A61B 17/00491 |
| 9,055,960 | B2 * | 6/2015 | Stoy ................. A61B 19/2203 |
| 9,204,879 | B2 * | 12/2015 | Shelton, IV ..... A61B 17/07207 |
| 2002/0032368 | A1 | 3/2002 | Takase |
| 2004/0102772 | A1 | 5/2004 | Baxter et al. |
| 2004/0225186 | A1 | 11/2004 | Horne, Jr. et al. |
| 2005/0096694 | A1 | 5/2005 | Lee |
| 2005/0216018 | A1 | 9/2005 | Sennett |
| 2005/0216033 | A1 | 9/2005 | Lee et al. |
| 2006/0178556 | A1 | 8/2006 | Hasser et al. |
| 2007/0010823 | A1 | 1/2007 | Kucklick |
| 2007/0118135 | A1 | 5/2007 | Mansmann |
| 2007/0219539 | A1 | 9/2007 | Efinger et al. |
| 2007/0282371 | A1 | 12/2007 | Lee et al. |
| 2008/0077146 | A1 | 3/2008 | Pernsteiner et al. |
| 2008/0234545 | A1 | 9/2008 | Breedveld et al. |
| 2009/0299343 | A1 | 12/2009 | Rogers |
| 2010/0151161 | A1 | 6/2010 | Da Rolo |
| 2010/0286694 | A1 | 11/2010 | Rio et al. |
| 2011/0004157 | A1 | 1/2011 | Dewaele et al. |
| 2011/0034764 | A1 | 2/2011 | Verbeek |
| 2012/0116163 | A1 | 5/2012 | Lutze et al. |
| 2012/0130173 | A1 | 5/2012 | Lutze et al. |

FOREIGN PATENT DOCUMENTS

| | | |
|---|---|---|
| DE | 695 17 463 | 3/2001 |
| DE | 10 2004 046 539 | 4/2006 |
| DE | 20 2009 007 979 | 9/2009 |
| DE | 20 2009 012 795 | 2/2010 |
| DE | 20 2009 012 698 | 6/2010 |
| EP | 0 445 918 | 9/1991 |
| EP | 0 626 604 | 11/1994 |
| EP | 0 677 276 | 6/2000 |
| EP | 0 986 989 | 1/2002 |
| EP | 1 243 283 | 9/2002 |
| EP | 0 840 572 | 10/2004 |
| EP | 0 764 423 | 3/2010 |
| WO | WO 93/13713 | 7/1993 |
| WO | WO 99/15090 | 4/1999 |
| WO | WO 2005/067785 | 7/2005 |
| WO | WO 2006/113216 | 10/2006 |
| WO | WO 2007/039875 | 4/2007 |
| WO | WO 2007/146842 | 12/2007 |
| WO | WO 2009/088430 | 7/2009 |
| WO | WO 2009/098244 | 8/2009 |
| WO | WO 2009/112060 | 9/2009 |
| WO | WO 2011/162853 | 12/2011 |

\* cited by examiner

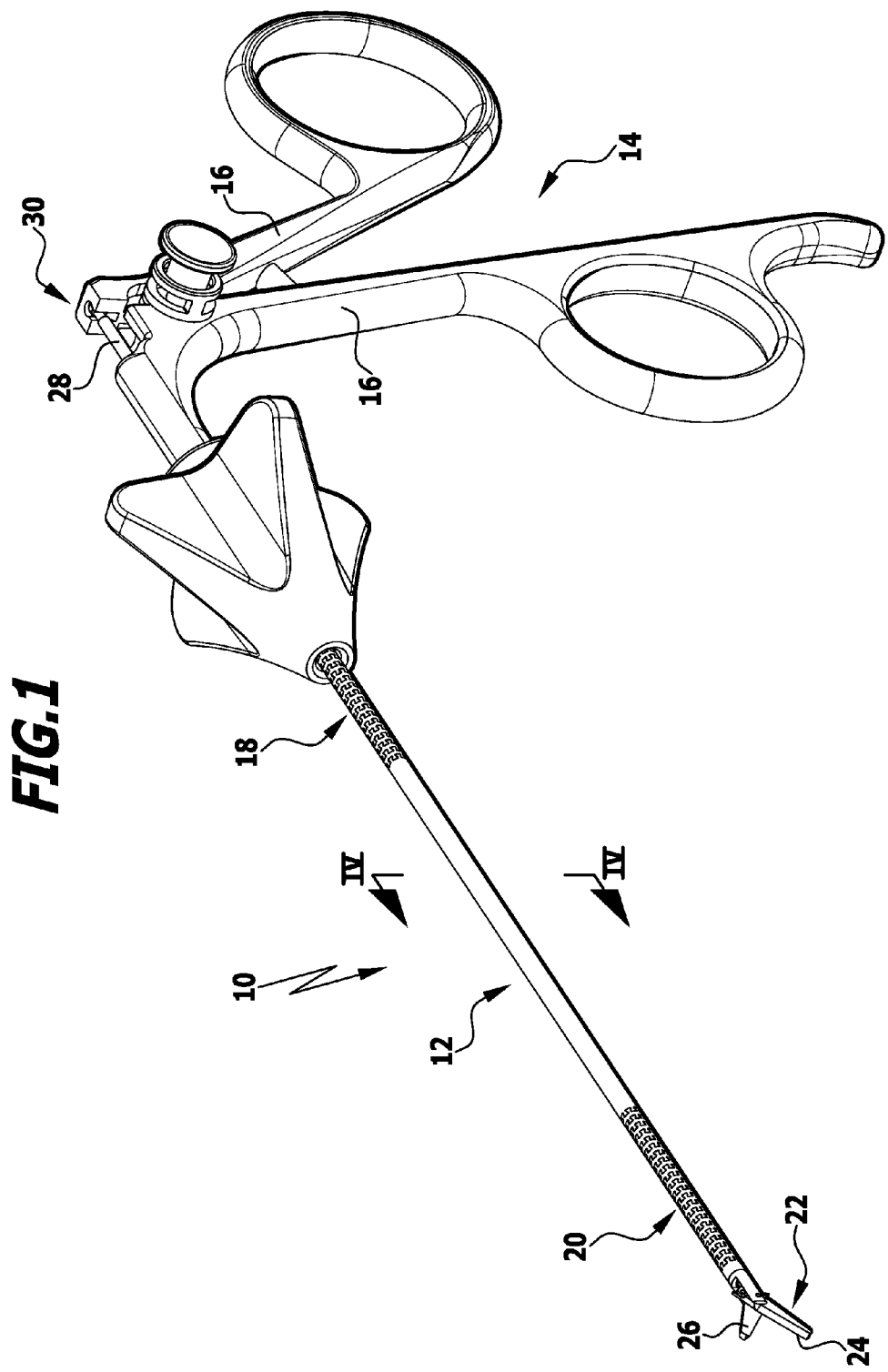

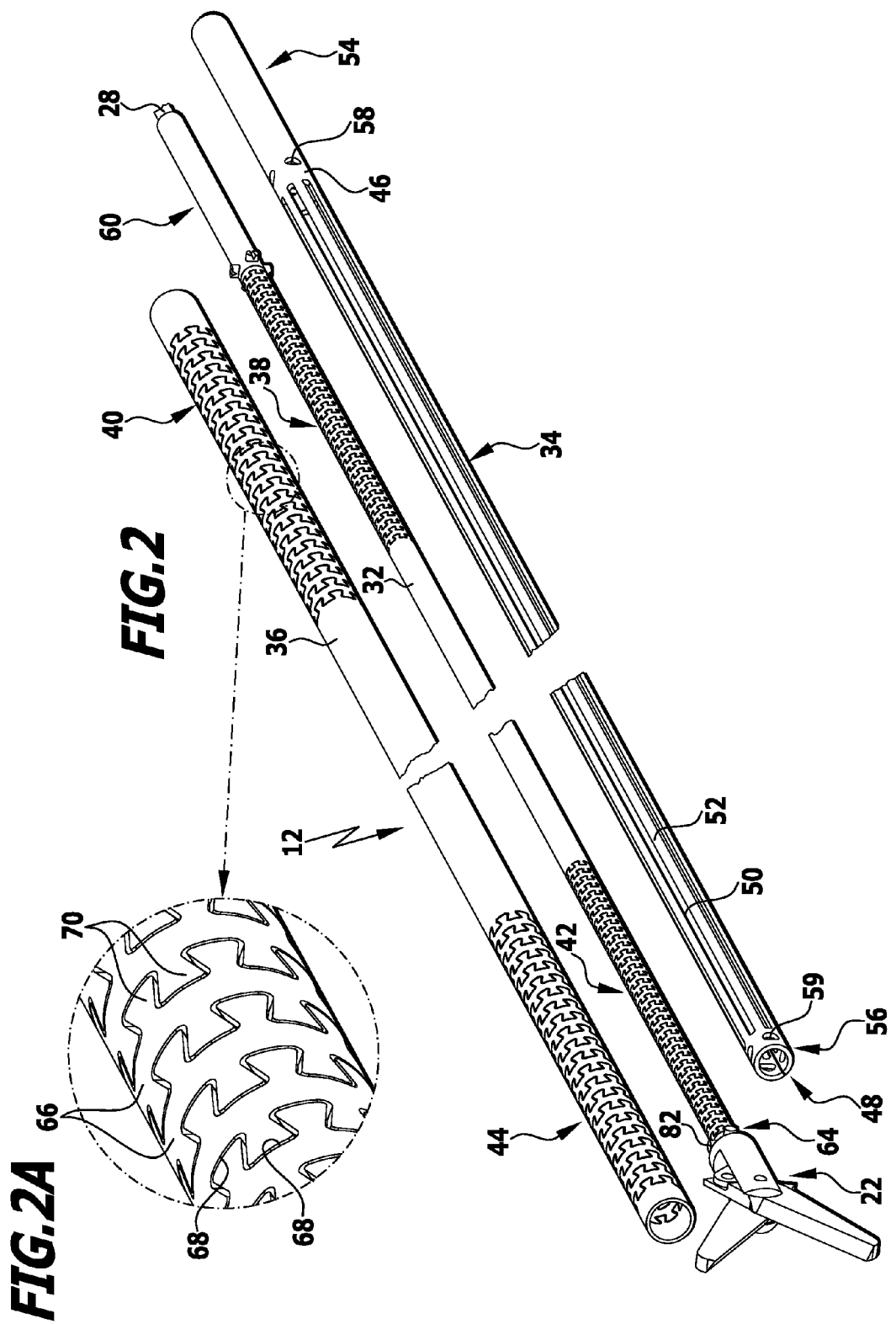

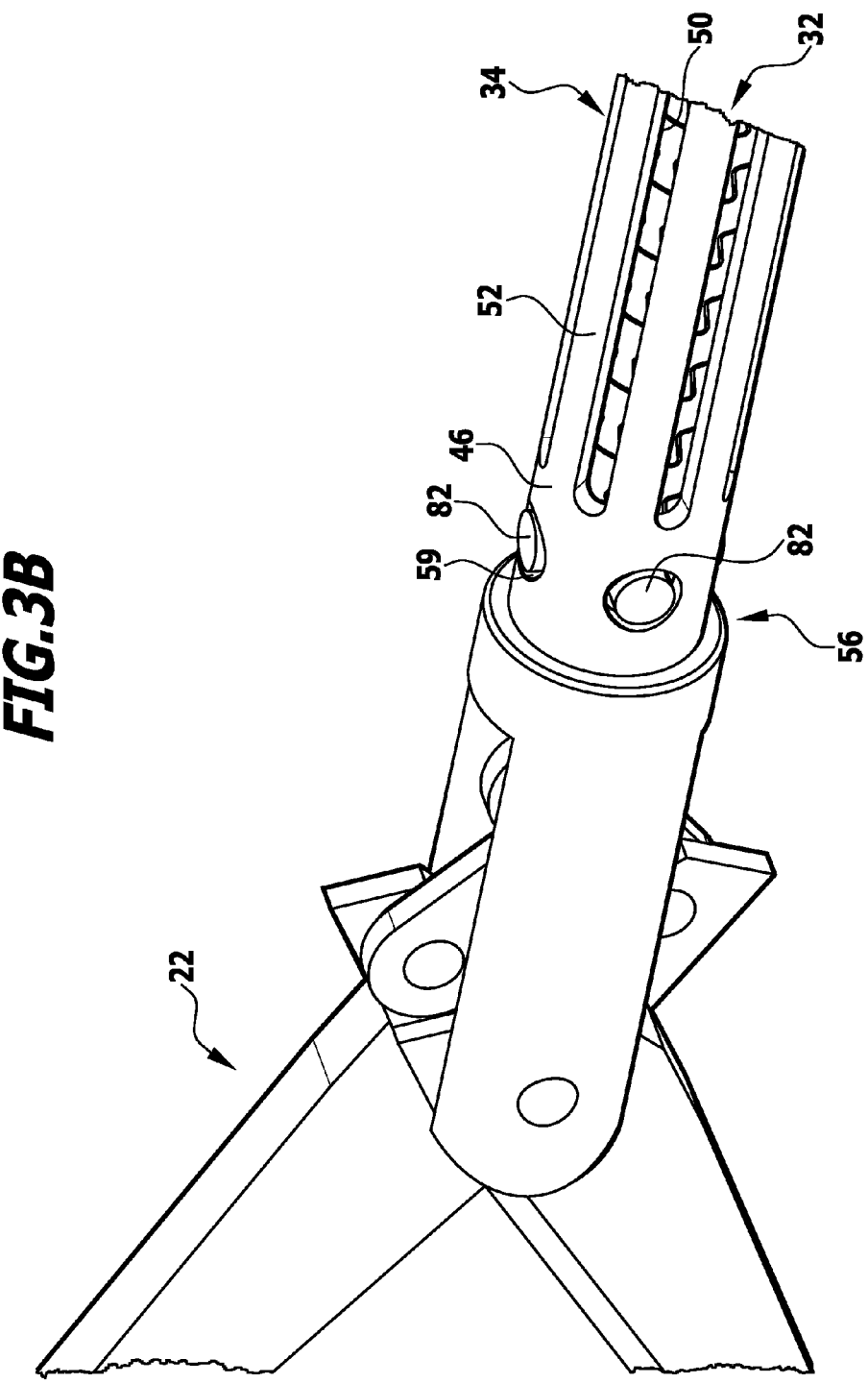

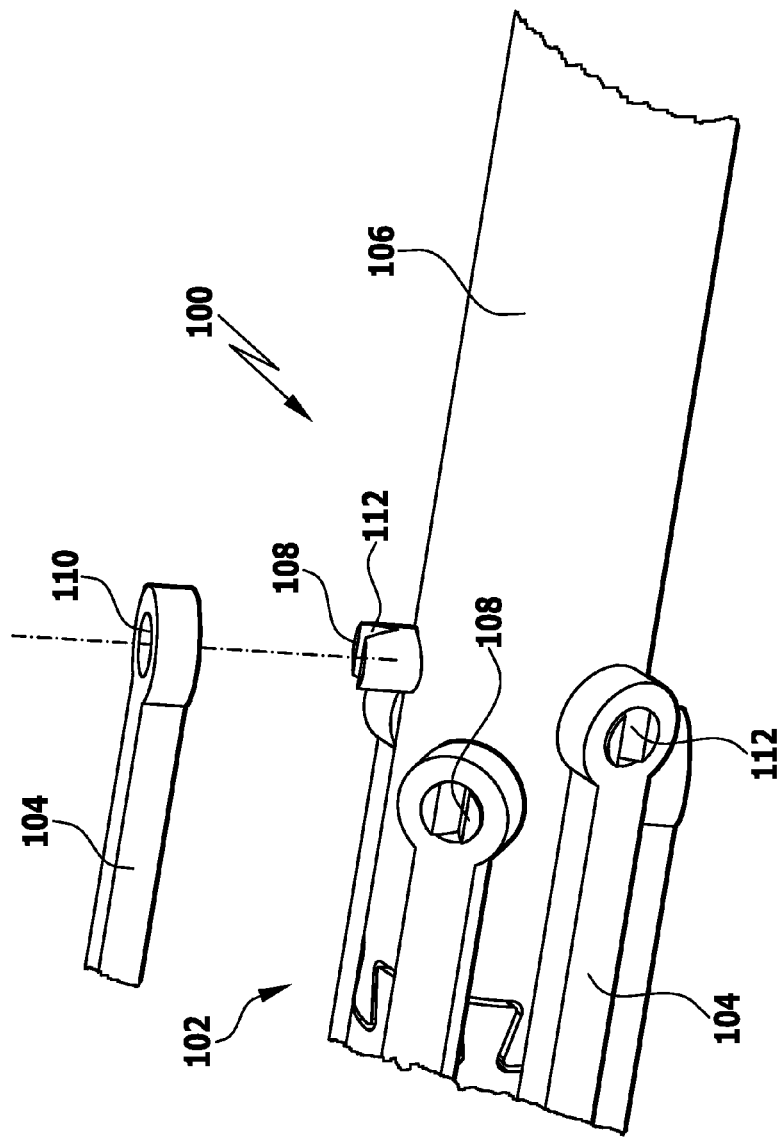

CONTROL APPARATUS

This application is a continuation of international application number PCT/EP2012/055114 filed on Mar. 22, 2012 and claims the benefit of German application number 10 2011 001 973.1 of Apr. 12, 2011, which are incorporated herein by reference in their entirety and for all purposes.

BACKGROUND OF THE INVENTION

The invention relates to a control apparatus for precision-mechanical applications or for surgical applications, for example for use in endoscopes or the like.

More particularly, the invention relates to a control apparatus for instruments for high-precision mechanical applications or for surgical applications in the minimally invasive field.

Such control apparatuses are known from prior art and have a proximal end section, meaning an end section facing towards the user/surgeon, and an end section distal to or facing away from the user/surgeon, each of which comprises an articulation zone, and a central section which is arranged between said end sections and is frequently configured to be flexurally rigid. The control apparatuses further comprise an outer hollow-cylindrical shaft, an inner hollow-cylindrical shaft and a control element which is arranged between said shafts and has two or more force-transmitting longitudinal elements which extend substantially from the proximal to the distal end section of the control apparatus. The force-transmitting longitudinal elements are arranged substantially regularly in a circumferential direction of the control apparatus and are interconnected in the area of the proximal and the distal end sections thereof in each case in a circumferential direction. Via the longitudinal elements, tension and preferably also compression forces can be transmitted with which a pivotal movement of the proximal end section can be translated into a correlating pivotal movement of the distal end section.

Generally, the proximal end of the control apparatus described at the outset has mounted thereto a manually operated handle part which can, of course, be replaced by motor-driven operating elements, whereas the distal end, also referred to as a head, can have tools, cameras, illuminating elements and the like connected thereto.

With such instruments that incorporate the control apparatus, it is possible in the mechanical field to inspect and repair for example intricate and difficult-to-access interiors of for example engines, machines, radiators and the like, or, in the surgical field, to perform the above-mentioned operations utilizing minimally invasive techniques.

Control apparatuses of the type mentioned at the outset are known for example from WO 2005/067785 A1, which uses a multiplicity of force-transmitting longitudinal elements in the form of wires or cables that are arranged in direct contact with one another in a circumferential direction, thus guiding one another laterally. The outer and inner hollow-cylindrical shafts are available to provide for guidance of the force-transmitting longitudinal elements in a radial direction so that guidance of the force-transmitting longitudinal elements is ensured in each direction.

Working in a similar way, the control apparatuses disclosed in WO 2009/098244 A2 use a slotted tube as a control element instead of the cables or wires. The control element comprises a multiplicity of longitudinal elements defined by slots in the tube and held together by unslotted end portions of the tube.

For the function of the control element described in WO 2009/098244 A2, it is important for the longitudinal elements to be wire-shaped, and hence flexible, in the articulation zones of the control apparatus and to be resistant to bending in the central section interposed between the articulation zones.

While a control element fabricated out of a tube has certain advantages in assembly of the control apparatus, the slotted tube is, on the other hand, elaborate to manufacture, in particular because the central section of the longitudinal elements has to be flexurally rigid.

In the latter regard, the concept described in WO 2009/112060 is more advantageous in that it eliminates the need for the flexurally rigid central sections of the longitudinal elements. But here, too, the function of force transmission via the longitudinal elements requires that these be mutually laterally guided, and this is associated with the occurrence of additional frictional forces.

The control apparatuses known heretofore have, by virtue of their construction principle, the disadvantage that when actuated, frictional forces operate between the longitudinal elements which act to fatigue the user, for example, the surgeon, at least over prolonged periods of use. This is particularly disadvantageous because it puts the patient at risk.

It is an object of the invention to propose a control apparatus which allows the user to work over a prolonged period of time without fatigue.

SUMMARY OF THE INVENTION

The invention relates to a control apparatus, in particular for use in endoscopes or the like, comprising a proximal and a distal end section, each of which comprises an articulation zone, and a central section arranged therebetween, and an outer hollow-cylindrical shaft, an inner, preferably hollow-cylindrical shaft, and a control element which is arranged between said shafts and has two or more force-transmitting longitudinal elements extending substantially from the proximal to the distal end section of the control apparatus for mechanically coupling the movement of the distal end section with the movement of the proximal articulation section, wherein the longitudinal elements are arranged in spaced-apart relation to one another at substantially regular angular distances $b_{1, 2} \ldots b_n$ in a circumferential direction of the control apparatus and are fixed relative to one another in the area of the proximal and the distal end sections thereof in each case in a circumferential direction and wherein the angular distances $b_{1, 2} \ldots b_n$ of the longitudinal elements relative to one another, as measured in a circumferential direction, are selected such that the force-transmitting longitudinal elements are guided without contact in a circumferential direction and optionally guided in contact with the outer and/or the inner shaft in a radial direction.

The control apparatus constructed in accordance with the invention thus enables a user to work without fatigue since the frictional forces acting on the longitudinal elements are substantially reduced as compared to conventional control apparatuses. Furthermore, the risk of material abrasion is reduced.

DETAILED DESCRIPTION OF THE INVENTION

In accordance with the present invention, it is possible to limit the guiding of the longitudinal elements to contact with the outer and/or the inner shaft, thus further reducing the frictional forces.

The longitudinal elements can have substantially the same flexibility both in the articulation zones and in the central section and can in particular be of the same flexibility over substantially their whole length. This allows longitudinal elements to be used that are cost-effective to manufacture.

However, for control apparatuses that are required to transmit greater forces during operation, it is preferred for the longitudinal elements to be in contact with and guided by the outer and the inner shaft in a radial direction.

This provides assurance that a precise sequence of motions is ensured even if the forces acting on the longitudinal elements could cause the longitudinal elements to undergo a slight elastic deformation.

If two force-transmitting longitudinal elements are used, the pivotal movement is restricted to one plane. If a plurality, in particular four, force-transmitting longitudinal elements are used, it is possible to pivot the control apparatus in two planes perpendicular to each other, or, in particular in those instances where six control elements or more are used, for example eight control elements, it is possible to pivot the control apparatus in planes which can be selected practically arbitrarily.

The cross-section of the longitudinal elements is configured preferably substantially in the shape of a circular arc segment or, more preferably, substantially in the shape of a rectangle.

While the circular arc segment shape provides an enhancement in the transverse rigidity of the longitudinal elements, the substantially rectangular cross-section of the longitudinal elements has the advantages of showing good transverse rigidity as well as minimizing the contact areas of the longitudinal elements relative to the one or more guiding outer and/or inner shaft(s).

There are several possible preferred ways in which the longitudinal elements to be used in accordance with the invention or the control element formed therefrom can be produced.

First, the control element with its longitudinal elements can be formed by a longitudinally slotted tube, preferably wherein the end portions of the tube remain unslotted, thus fixing the longitudinal elements relative to one another in a circumferential direction. Preferably, the slots are formed in the wall of the tube in a radial direction thereof, for example by laser cutting. Depending on the elasticity of the tube material and the cutting technique used, the resulting kerfs can be dimensioned such as to already obtain sufficient angular distances between the longitudinal elements in order to maintain the non-contacting relation therebetween even under the action of forces. Here, the longitudinal elements take the form of a circular arc in cross-section.

In terms of manufacture, the control element to be used in accordance with the invention is simpler to produce if one uses a longitudinally slotted sheet material that is only later formed into a tube. Apart from the above-mentioned advantage in terms of manufacture, this has the further advantage of substantially greater choice of raw materials, and these can be procured at lower prices. Furthermore, the sheet materials can be manufactured to smaller tolerances than the first-mentioned tubes.

Finally, the longitudinal elements that are fabricated from the sheet material have, in lieu of the circular arc-shaped cross-section, a substantially rectangular cross-section in which the contact areas with the guiding shafts and hence the frictional forces during operation of the control apparatus are considerably reduced further, as has already been mentioned.

The end portions of the sheet material in an axial direction can remain unslotted so that the longitudinal elements are already fixed relative to one another in a circumferential direction. In this case as well, the kerfs between the longitudinal elements that are produced when making the slots can provide sufficient angular distances in the finished control element, depending on the material and production technique used.

Alternatively, the longitudinal elements are preferably initially fabricated as individual rod-shaped elements made from a sheet material, these being fixed relative to one another at their proximal and distal ends in a circumferential direction, for example by use of an annular collar. This provides the same benefits as with the control element fabricated out of a sheet material as described above. An additional advantage is that different techniques that are tailored to the particular application of the control apparatus can be used for the fixation of the longitudinal elements relative to one another in a circumferential direction, as will be discussed in more detail in connection with the description of the figures. If an annular collar is used, this can also be manufactured to a complex design for form-locking engagement with the ends of the longitudinal elements, for example by an erosion process or by powder injection moulding (PIM). Also preferred are annular collars made of oxide ceramics.

The control element need not necessarily be in contact with the inner and outer shafts. Rather, it is preferred that a gap be provided on at least the inner or the outer side of the control element relative to the outer surface of the inner shaft and the inner surface of the outer shaft respectively which preferably amounts to approximately 0.01 to 0.5 mm in the resting position of the control element.

For further optimization of their sliding performance against each other, the inner surface of the outer shaft, the longitudinal elements and/or the outer surfaces of the inner shaft may be coated with a material that reduces sliding friction, for example PTFE.

In a preferred control apparatus, the outside diameter of the outer shaft is in the range of approximately 1 mm to approximately 20 mm and the inside diameter of the inner shaft is in the range of approximately 0.05 mm to approximately 5 mm, in particular approximately 0.2 mm to approximately 5 mm.

In many instances, these dimensions are typical for control apparatuses to be used in endoscopy and permit the use of instruments and tools that can be arranged at the distal end of the control apparatus and can be controlled and actuated via the lumen of the inner shaft.

It will be understood that it is of course conceivable in the case of other applications to have control apparatuses with dimensions that differ considerably from the values in the aforementioned ranges.

In many cases, the longitudinal elements of the control element may be of straight configuration. Movement of the proximal end section is then translated into a corresponding pivotal movement of the distal end section which is performed in the same plane as that of the proximal end and in the same direction of pivoting.

While for many applications this sequence of motions provides adequate access to the particular sites of use of the instruments and tools arranged on the control apparatus, there are applications in which it is desirable to have a different type of translation of the movements of the proximal and distal end sections.

To this end, the present invention proposes that the distal ends of the longitudinal elements be fixed in a circumferential direction in angular positions that are different from the angular positions in which are fixed the proximal ends associated with them in each case, wherein the angular positions preferably differ in a circumferential direction by approximately 10° to 350°, in particular by approximately 45° to 315°, more preferably in the range of approximately 150° to approximately 210°. The pivotal movements of the distal and proximal end sections then no longer take place in the same plane and/or in the same direction of pivoting.

Of particular importance are control apparatuses constructed in accordance with the present invention in which the angular positions have a difference of approximately 180° so that a mirror-inverted movement of the proximal and distal end sections in one plane can be generated.

The arrangement of the longitudinal elements in a circumferential direction for achieving the different angular positions at the proximal and the distal end can be accomplished in different ways.

In connection with such an embodiment, provision may in particular be made for the force-transmitting longitudinal elements to be arranged in the shape of a helix between the shafts over at least part of their length.

In a preferred embodiment, the force-transmitting longitudinal elements are arranged in the shape of a helix between the shafts over their entire length. With respect to the typical length of the control apparatus of 10 cm and considerably more and with a typical diameter of a few millimeters, this results in an extremely high pitch of the helix shape or, stated differently, a very slight deviation from parallelism relative to the longitudinal direction of the control apparatus, amounting to a few angular degrees, for example approximately 5° or less.

In accordance with a variant of this embodiment, the force-transmitting longitudinal elements are arranged substantially parallel to the longitudinal direction of the control apparatus in the area of the proximal and/or the distal end and are arranged in the form of a helix in an area located therebetween.

In accordance with a further variant, the force-transmitting longitudinal elements have one or more sections in the area between their proximal and distal ends which are arranged parallel to the longitudinal direction of the control apparatus. Other sections, particularly adjacent to the proximal and the distal end, are arranged in the shape of a helix.

Although in the case of the latter two variants only part of the entire length of the control element is available for achieving the angular offset, it is still the case that only slight angular deviations from the longitudinal direction are necessary, for example approximately 5° or less.

There are a variety of ways which lend themselves to achieving the configuration of the articulation sections.

To this end, the prior art has proposed shaft sections that are slotted in a circumferential direction in a variety of patterns, as set forth for example in U.S. Pat. No. 5,741,429.

Similar proposals for the configuration of the articulation sections can also be found in WO 2009/098244 A2 and WO 2009/112060 A1.

Here, the articulation zone(s) of the outer and/or the inner shaft may comprise a wall section in which are arranged a plurality of slots spaced apart from one another and extending in a circumferential direction and preferably configured as slots extending completely through the cylindrical wall of the shaft, preferably wherein two or more, in particular three or more, slots are arranged one behind the other in a circumferential direction.

Preferred articulation zones of this embodiment have, in an axial direction, three or more slots arranged side by side and optionally offset relative to one another.

Provision may be made for at least one of the articulation zones to be configured to be elastic so that a restoring effect exerted by the control element is enhanced.

While these embodiments of the articulation sections known per se are quite suitable for use with the control apparatus constructed in accordance with the invention, in alternative embodiments the articulation sections are configured such that they comprise for the inner and/or the outer shaft a plurality of separate annular segments, each of which has a first and a second end region in an axial direction, wherein the first end region comprises two or more projections projecting in an axial direction and the second end region comprises two or more recesses receiving said projections, wherein the projections and recesses are arranged at regular distances in a circumferential direction on the respective annular segment, wherein the annular segments are in articulating engagement with one another via the projections and recesses and wherein the annular segments are connected together in a form-locking manner via the projections and recesses in an axial direction and/or a radial direction.

With this type of articulation sections, the expenditure of force for actuating the control apparatus is considerably reduced.

The control element configured in accordance with the invention may be formed with longitudinal elements that are capable of being elastically deflected from the axial direction and exert a restoring force in the articulation sections that is sufficient for the control apparatus as a whole. The articulation sections of the outer and inner shafts need not contribute to the restoring function. The form-locking engagement of the adjacent annular segments is a loose interengagement of projections and recesses.

The projections and recesses are typically arranged at regular intervals in a circumferential direction of the shafts.

By choosing an odd number of projections and recesses, it is ensured that the articulation sections or the annular segments thereof are mechanically secured and the individual segments are captively integrated. This enables simplified assembly of the control apparatus.

In addition or alternatively, provision may be made for the recesses to have on the radially inner side in a circumferential direction an extension that is smaller than the corresponding radially outer extension of the projection that engages in the recess.

More preferred control apparatuses involve the projections having, in a circumferential direction, a greater extension at the free end thereof facing away from the annular segment than adjacent to the annular segment, and the recesses having, in a circumferential direction, an extension at the open end thereof that is smaller than the extension of the projection engaging in the recess at the free end thereof.

Securing the annular segments relative to each other can already be accomplished by this measure alone.

More preferably, the projections and recesses are configured to have an essentially trapezoidal shape in cross-section in a circumferential direction and/or a radial direction.

Preferred materials for producing the longitudinal elements of the control element comprise steel alloys and Nitinol.

For some applications, the control apparatus may be configured to be flexible along its whole length so that a straight access channel is not essential when inserted into the operating field. For high-precision tasks, however, it is often desirable for at least one of the outer and the inner shaft to have a flexurally rigid section arranged between the proximal and distal articulation zones.

Typically, the control apparatus is configured to be flexurally rigid in its central section.

In accordance with an embodiment of the invention, at least one of the outer and the inner shaft is provided with a flexurally rigid section in the area between the proximal and distal articulation zones, said flexurally rigid section implementing the flexural rigidity of the central section of the control apparatus.

While in many instances the proximal and the distal articulation zone are of the same configuration and in particular have an equal extension in a longitudinal direction of the control apparatus, this is not absolutely essential.

In particular, provision may be made for the proximal and the distal articulation zone to be of different configuration, in particular to differ in length, so that a corresponding pivotal movement of the proximal articulation zone results in a reduced or increased pivotal movement of the distal end section.

In particular, provision may be made for the pivotal movement of the proximal and/or the distal articulation zone to be adjustable. This may be accomplished for example by varying the extension of the proximal and/or the distal articulation zone and thus the pivoting behaviour of the two articulation zones relative to each other.

In particular, provision may be made for the control apparatus to comprise a holding device by virtue of which parts of one of the articulation zones are capable of being fixed in a flexurally rigid manner relative to the central section of the control apparatus or a functional unit adjoining the proximal or distal end section thereof.

Thus, in a variation of the control apparatus constructed in accordance with the invention, the holding device can comprise a flexurally rigid sleeve which is capable of being displaced parallel to the longitudinal axis of the central section, which in this case is configured to be flexurally rigid.

Depending on the position of the sleeve in a longitudinal direction relative to the central section, the proximal and/or the distal end section and the articulation zone provided there can be influenced in their length and hence also in their pivoting behaviour.

Preferably, the flexurally rigid sleeve is arranged on the outer circumference of the flexurally rigid shaft so that the lumen of the control apparatus remains unaffected. If for certain application cases the lumen of the control apparatus is sufficiently large, it is of course also possible for a flexurally rigid sleeve to be arranged inside the lumen. However, the capability for displacement, and in particular also the fixation, of the flexurally rigid sleeve are easier to implement when same is arranged on the outer circumference of the outer shaft.

In accordance with another variant, the holding device can comprise a supporting holding element on the functional unit coupled to the proximal or the distal end of the control apparatus. In this way, the articulation zone can be influenced in its pivoting behaviour from the distal or the proximal end side.

In accordance with another variant of the control apparatus constructed in accordance with the invention, the holding device is capable of being positioned, and in particular also fixed, in a predetermined position. This provides the possibility of preadjusting or readjusting the pivoting behaviour of the distal and proximal end sections relative to each other in a repeatable and precisely predeterminable manner.

In accordance with a further variant of the control apparatus constructed in accordance with the invention, provision is made for at least one of the articulation zones to be of elastic configuration so that when the forces introduced for pivoting the end sections relax, the control apparatus reassumes its original, straight position.

These and further advantages of the invention are described in more detail below with reference to the drawing.

BRIEF DESCRIPTION OF THE DRAWINGS

FIG. 1 shows a perspective view of a surgical instrument including a control apparatus constructed in accordance with the invention;

FIG. 2 depicts an exploded view of the control apparatus of FIG. 1;

FIG. 2A shows a detail of an articulation zone of the apparatus illustrated in FIG. 2;

FIGS. 3A and 3B are details of portions of the control apparatus of FIG. 2;

FIGS. 5A to 5C are details of an alternative control apparatus constructed in accordance with the invention;

DETAILED DESCRIPTION OF THE DRAWINGS

Figure 3A:
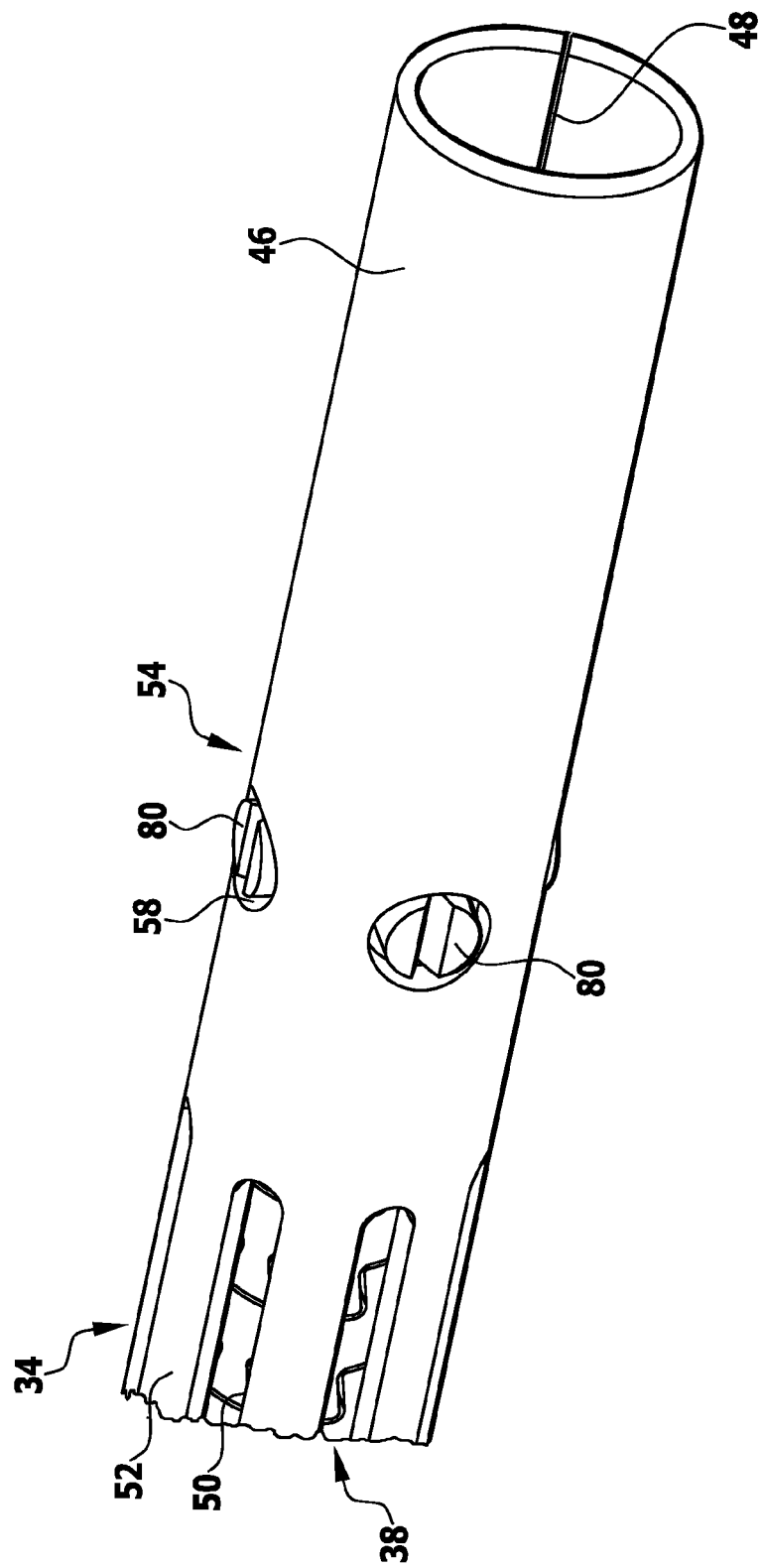

FIG. 1 shows a surgical instrument, designated generally by reference character 10, including a control apparatus 12 constructed in accordance with the invention and a handle 14 having two arms 16 that are capable of being pivoted relative to each other, said handle 14 being detachably connected to a proximal end 18 of the control apparatus 12.

Fixed at a distal end 20 of the control apparatus 12 is a cutting tool 22 whose shear blades 24, 26 are mounted for pivotal movement relative to each other. The pivotal movement of the shear blades 24, 26 is effected via the pivoting of the arms 16, wherein pivotal movements of the arms 16 are transmitted to the shear blades 24, 26 of the cutting tool 22 via a cylindrical coupling element 28 guided within the control apparatus 12. At a proximal end, the coupling element 28 is detachably connected to one of the arms by a locking fit 30, while its distal end (not shown) is connected to a pivoting mechanism (not shown) of the cutting tool 22 in a manner known per se.

FIG. 2 shows in detail the control apparatus 12. The control apparatus 12 comprises an inner shaft 32, a control element 34 and an outer shaft 36. The coupling element 28 is guided inside the inner shaft.

The inner and outer shafts 32, 36 are each formed with proximal and distal articulation zones 38, 40 and 42, 44 respectively.

In the embodiment illustrated here, the control element 34 is formed from a strip-shaped sheet material 46 formed into a tube and having its lateral ends joined together in the area designated by reference character 48. Said lateral ends can be joined together loosely or can be secured by a seam 48, for example by way of welding or adhesive bonding.

The strip-shaped sheet material 46 is provided lengthwise with slots 50 defining a distance between longitudinal elements 52. The slots 50 extend between a proximal end portion 54 of the sheet material and a distal end portion 56 thereof.

The end portions 54, 56 remain unslotted, thus connecting the longitudinal elements 52 at the proximal and distal ends thereof in the form of an annular collar.

The slots extend into and optionally beyond the articulation zones of the inner and outer shafts. It is thus ensured that the articulating function of the articulation sections is assisted by the control element 34 without taking any further measures.

The proximal end portion 54 is provided with bores 58 which allow mechanical connection to the proximal end portion 60 of the inner shaft 32. This distal end portion 56 is likewise provided with bores 59 which allow mechanical connection of the distal end portion 56 of the control element 34 to the distal end portion 64 of the inner shaft 32.

The mechanical connection may be effected by a mere form-locking engagement or may also be a substance-to-substance-bond produced for example through adhesive bonding or welding.

The proximal and distal articulation sections 38, 40 and 42, 44 of the inner and outer shafts 32, 36 can be of the same configuration.

In the present exemplary embodiment, the articulation sections 38, 40, 42, 44 are each formed from a plurality of annular segments 66, as may be seen in the enlarged view of FIG. 2A. The annular segments 66 have, at one axial end thereof, recesses 68 regularly distributed about the circumference thereof, while the other axial end thereof is formed with projections 70. The recesses 68 and the projections 70 are configured complementary to each other so that a form-locking engagement results. Preferably, the inner and outer shafts are made from one-piece tubes, with the articulation sections being produced for example by way of laser cutting. Choosing the number of projections and recesses to be odd, for example 7, ensures that the annular segments, after manufacture, are maintained in a captively connected relationship with respect to one another even with a loose engagement therebetween.

By using a trapezoidal shape for the projections and recesses 68, 70 in a circumferential and preferably also radial direction, a captive and yet articulating connection between adjacent annular segments 66 can also be established when using an even number of projections and recesses.

FIGS. 3A and 3B show once again details of the proximal and distal end portions respectively of the control apparatus 12 constructed in accordance with the invention.

FIG. 3A shows the control element 34 with the sheet material 46 formed into a tube, said control element 34 comprising six longitudinal elements 52 separated from one another by way of slots 50 and comprising the unslotted portion 54 having through-openings 58 provided therein which are essentially evenly distributed in a circumferential direction and receive projections provided at the proximal end portion 60 of the inner shaft 32 in radially outwardly projecting relation thereto. As shown in detail in FIG. 3A, the projections may take the form of screw heads 80.

Shown in the interior of the control element 34 is the articulation section 38 of the inner shaft 32, which is formed from annular segments 66 as described above.

FIG. 3B shows in detail the configuration of the distal end portion 56 of the control element 34 wherein, again, the distal end portion 56 has through-openings 59 provided therein which receive pin-like projections 82 formed at the distal end portion 64 of the inner shaft 32 when the sheet material 46 of which the control element 34 is made is formed into a tube. Screw heads as shown in FIG. 3A for the proximal end portion can replace the pin-like projections and vice versa.

As has previously been described, adjoining the distal end portion 56 of the control element 34 is the cutting tool 22, the specific configuration of which is known per se and need not be discussed in more detail here.

Also seen in FIG. 3B is the configuration of the distal articulation zone 42 of the inner shaft 32 wherein, again, annular segments 66 as described above are used in articulating engagement with one another.

In the surgical instrument illustrated in FIGS. 1 to 3, the control apparatus 12 is configured such that due to the elasticity of the longitudinal elements 52, which were fabricated out of the strip-shaped sheet material 46, a sufficient restoring force is made available so that the surgical instrument or the control apparatus 12 thereof has a straight configuration when in the unstressed condition.

If, at the proximal end 18 of the control apparatus 12, the handle 14 is for example deflected downwards relative to the longitudinal axis of the control apparatus 12 in FIG. 1, then this causes the distal end 20 of the control apparatus to be pivoted upwards at the same time and to the same extent. Upon release of the force exerted on the handle 14, the control apparatus 12 automatically returns to the straight configuration.

As mentioned above, the elasticity of the longitudinal elements 52 is responsible for the restoring effect, whereas the articulation sections 38, 40, 42, 44 of the inner and outer shafts 32 and 36 formed from annular segments 66 need not make a contribution thereto.

Figure 4A:
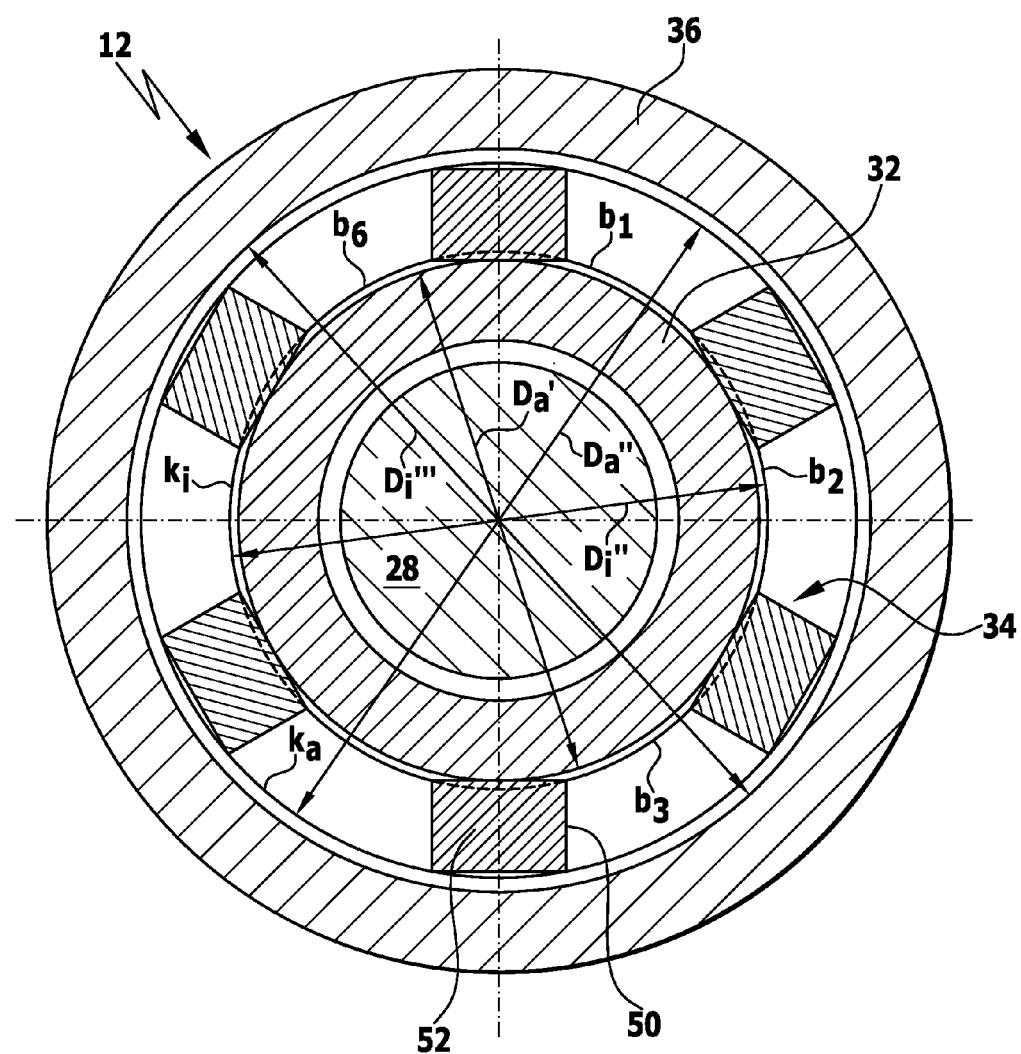
FIGS. 4A and 4B illustrate a sectional view taken along line IV-IV in FIG. 1 and an alternative embodiment thereof respectively.

A cross-sectional view of the control apparatus taken along line IV-IV of FIG. 1 is shown in FIG. 4A.

The control apparatus comprises, as viewed from the outside to the inside, an outer shaft 36 and an inner shaft 32 forming an annular space therebetween in which the control element 34 is received. Finally, arranged inside the inner shaft 32 is a flexible pull or push rod as a coupling element 28.

The six longitudinal elements 52 are separated from one another in a circumferential direction via slots 50 and are shown here only schematically in order to illustrate the principle of the design of the width of the longitudinal elements and the distance $b_1, b_2 \ldots b_6$ therebetween.

In FIG. 4A, the individual dimensions are designated as follows:

Da'=outside diameter of the inner shaft 32;
Di''=diameter of a circle $K_i$ running through the radially inner edges of the longitudinal elements 52;
Da''=diameter of a circle $K_a$ running through the radially outer edges of the longitudinal elements 52;
Di'''=inside diameter of the outer shaft 36;
$b_{1,2}, \ldots$ =distance of the longitudinal elements 52 from one another, as measured in a circumferential direction along the circle of diameter Di'.

It can be assumed under the forces typically occurring in the control apparatuses constructed in accordance with the invention and with the materials preferably used for making the control element 34 such as Nitinol that the material's elasticity does not lead to a change in length of the longitudinal elements 52.

Given this condition, the following relationship (1) then applies to the dimensioning of the outside diameter Da' with respect to the inside diameter Di" and the distances $b_1, b_2 \ldots b_n$ of the longitudinal elements 52 measured in a circumferential direction (in the special case of FIG. 4A, n=6):

$$Da' > Di'' - 1/n * \Sigma(b_1 + b_2 + \ldots b_n) \quad (1)$$

Preferably, the following relationship (2) is additionally satisfied for the diameters among themselves:

$$Di''' - Da' < 1\frac{1}{2} * (Da'' - Di'') \quad (2)$$

This also takes into account the fabrication tolerances for the individual shafts and longitudinal elements.

Figure 4B:
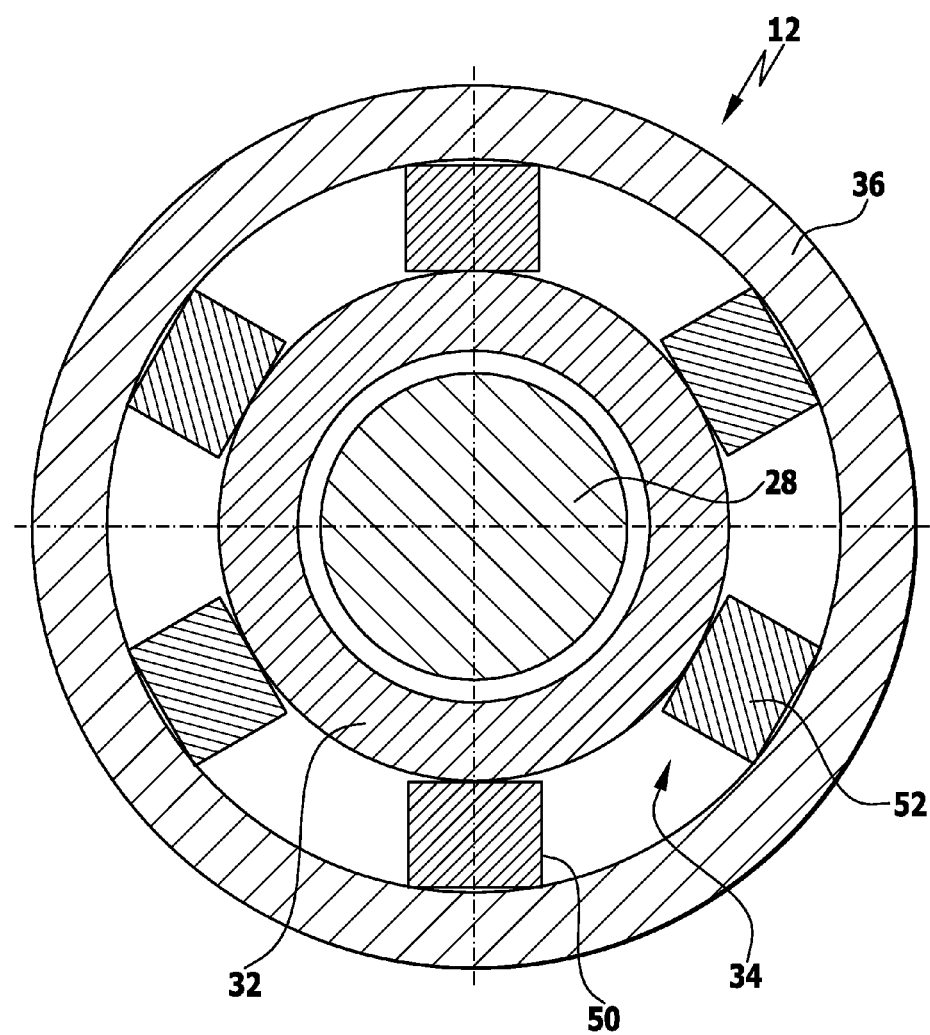

FIG. 4B illustrates a variant of the embodiment of FIG. 4A in which the longitudinal elements 52 are, at radially inner and outer edges thereof, guided by the inner and outer shafts 32, 36 respectively.

Figure 5A:
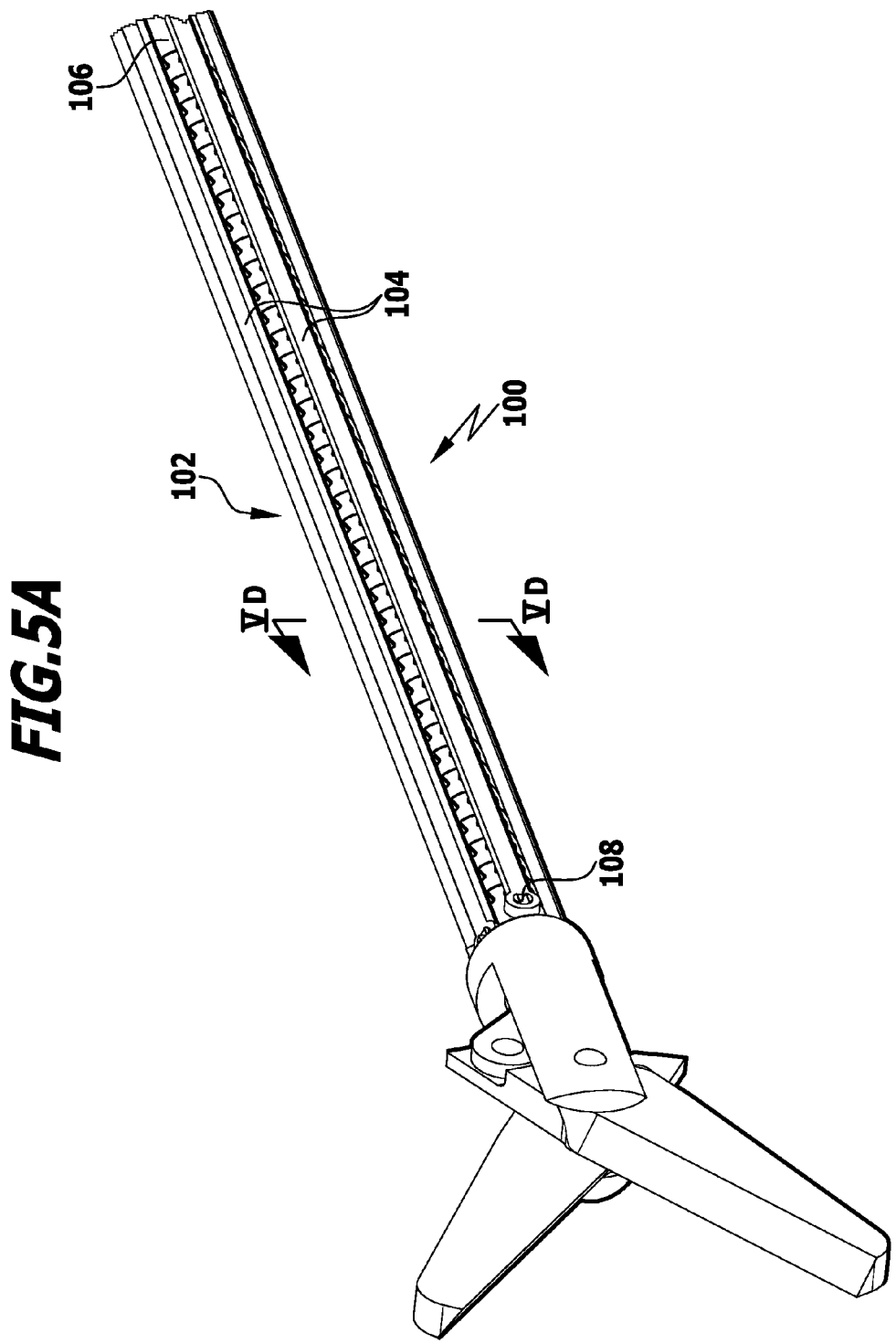
Figure 5B:
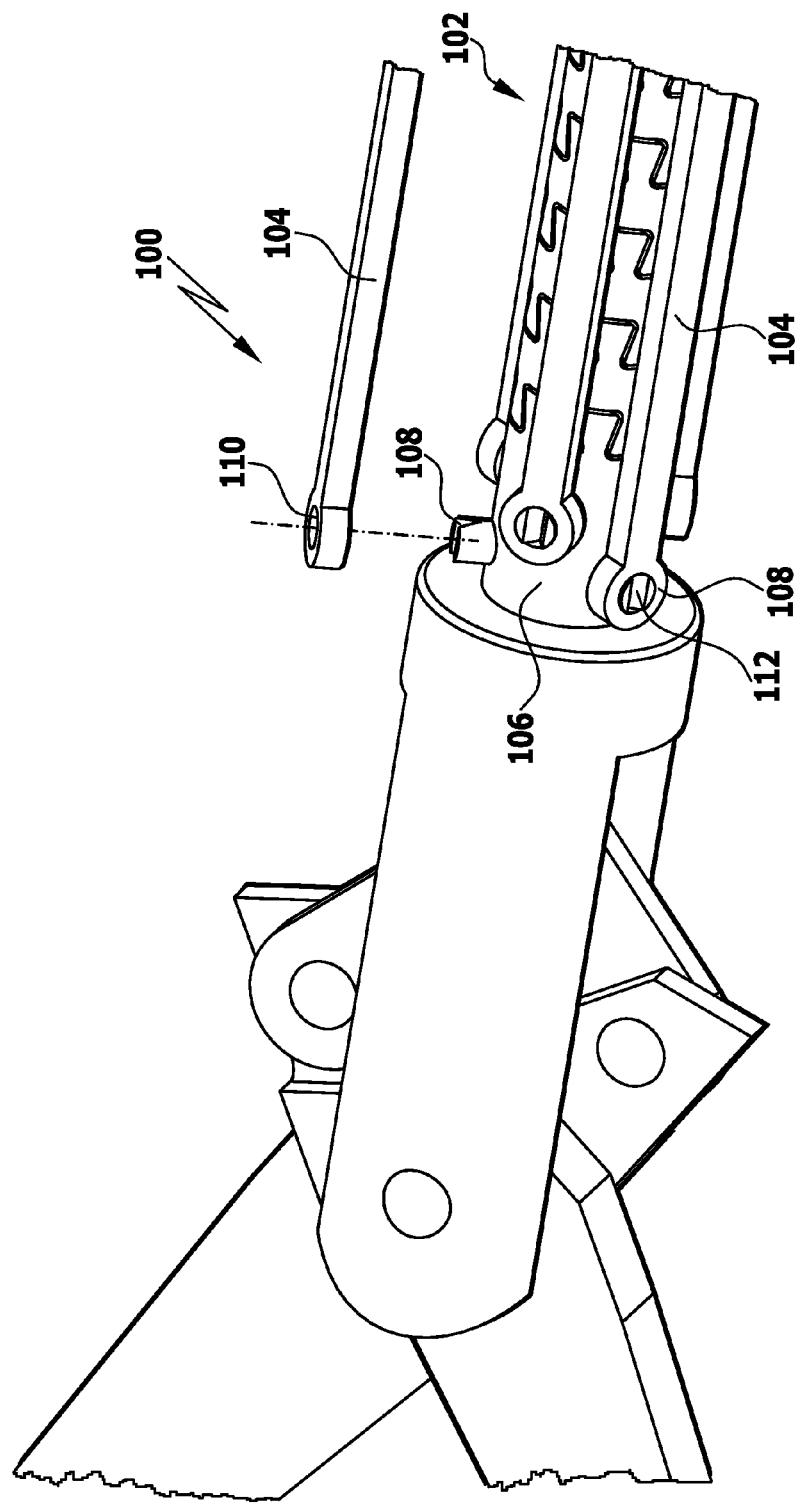

FIGS. 5A to 5C show an alternative control apparatus 100 having a control element 102 whose construction differs from that of the control element of the control apparatus 12 described in connection with FIGS. 1 to 4. Here, in lieu of a continuous sheet material, individual webs are used as longitudinal elements 104 which are fixed in a spaced-apart relationship at the proximal and distal ends thereof.

The fixation of the longitudinal elements 104 at a sufficient distance relative to one another can occur on a separate annular collar, or, as shown in the context of FIGS. 5A to 5C, said longitudinal elements 104 are preferably fixed at proximal and distal ends of the inner shaft 106. The inner shaft 106, as well as the associated outer shaft (cf. shaft 109 in FIG. 5D) not shown here for simplicity, can be constructed as described in connection with the inner and outer shafts of the control apparatus 12 of FIGS. 1 to 4.

For fixing the longitudinal elements 104 at the proximal and distal ends of the inner shaft 106, the latter may have projections 108 provided thereon, while the longitudinal elements 104 in each case are, at their proximal and distal ends, provided with an opening 110 into which the projection 108 can engage. Particular preference is given to the projections 108, as shown in FIGS. 5A and 5C in particular, which comprise a wedge-shaped groove 112 that can be spread open somewhat after placement of the longitudinal elements 104 so that in addition to the form-locking engagement between the projection 108 and the through-opening 110 there is a force-locking engagement that fixes the longitudinal elements 104 to the inner shaft 106 for the purposes of further assembly of the control apparatus. The force-locking engagement need not be particularly strong so that the longitudinal elements 104 are in particular disengageably mounted to the inner shaft 106, because in the completely assembled state of the control apparatus 100 an outer shaft 109 extends over the area of the projections 108 and the eyelets 110 at the respective ends of the longitudinal elements 104 whereby, as seen in the sectional view of FIG. 5D, the longitudinal elements 104 or the through-openings 110 thereof are maintained in permanent engagement with the projections 108.

With this solution as described and in particular in those instances where the number of longitudinal elements 104 is large, such as six or more like in the present example, the connection between the longitudinal elements 104 and the proximal and distal end portions of the inner shaft 106 is effected such that the projections 108 are arranged in a somewhat offset relationship to one another in a longitudinal direction, i.e., in an axial direction of the inner shaft 106, so that the enlarged regions of the longitudinal elements 104, which contain the eyelet 110, are capable of being mounted without mutual contact.

Figure 5D:
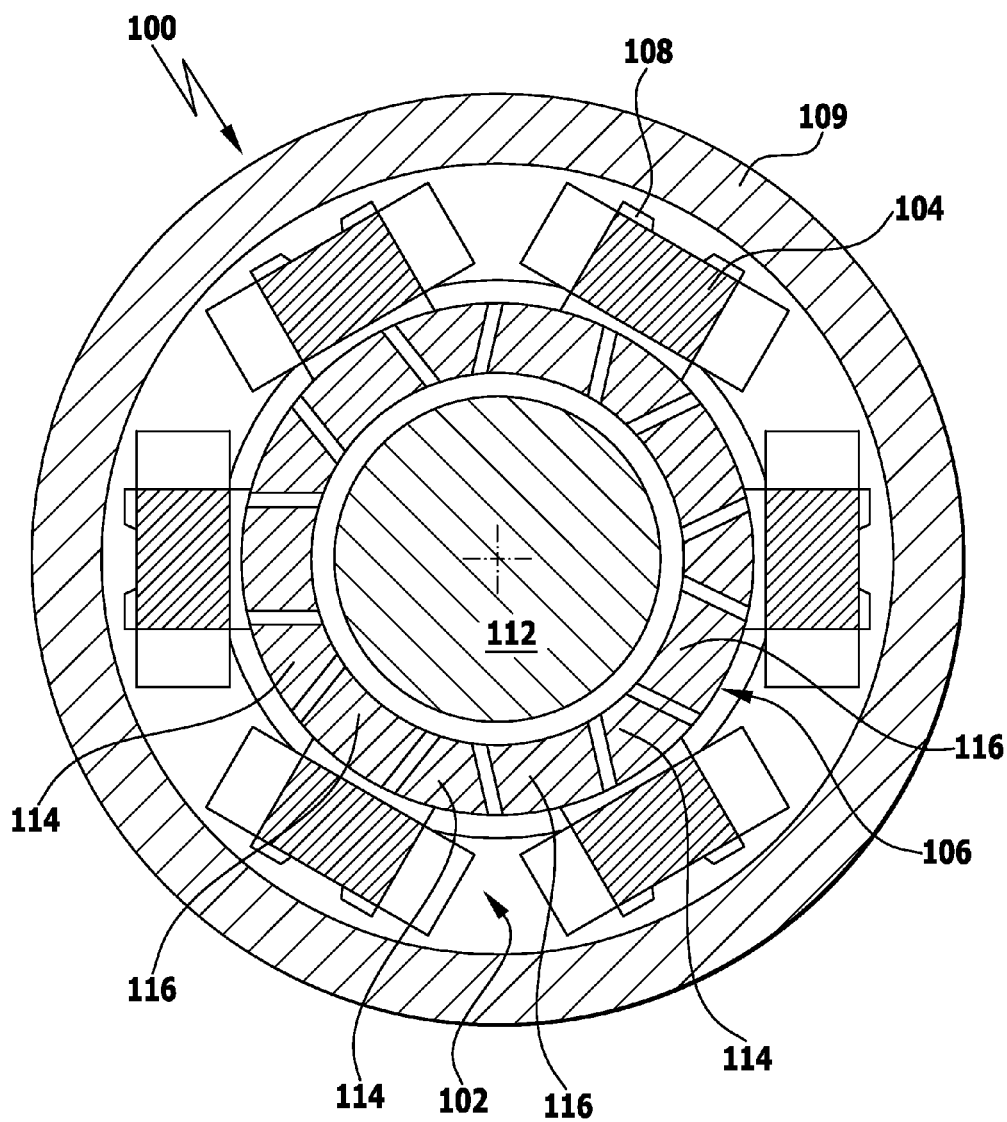
FIG. 5D is a cross-section taken along Line VD-VD of FIG. 5A with an added outer shaft.

FIG. 5D illustrates the control apparatus 100 of FIG. 5A in a cross-sectional view and in a completely assembled form, wherein, as viewed from the outside to the inside, an outer shaft 109 surrounds the inner shaft 106 and the control element 102, formed from individual longitudinal elements 104, and fixes the control element in its position. Also shown in the interior of the inner shaft 106 is a coupling element 112 which is similar to the coupling element 28 of the embodiment of FIGS. 1 to 4. Moreover, FIG. 5D also shows the annular elements 114 and 116, which are articulately connected to one another via projections and recesses. A corresponding construction can also be present in the outer shaft 109 (details of this are omitted from FIG. 5D).

Figure 6A:
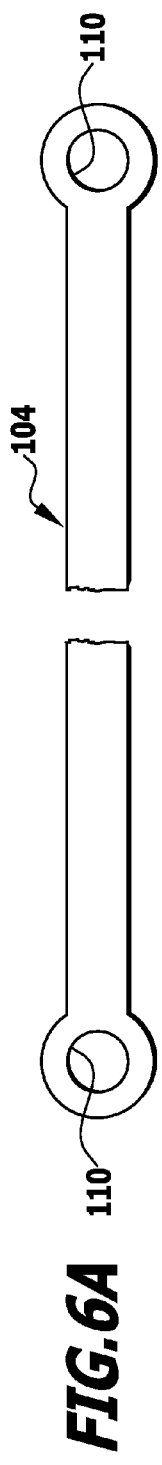
FIGS. 6A to 6E illustrate various alternative embodiments of longitudinal elements for forming a control element of a control apparatus constructed in accordance with the invention.

A large variety of variants lend themselves as alternatives to the longitudinal elements 104 for forming the control element 102 as described in FIGS. 5A to 5D, these being exemplified in FIGS. 6A to 6E, with FIG. 6A once again showing the longitudinal elements 104 to facilitate better comparison.

Figure 6B:
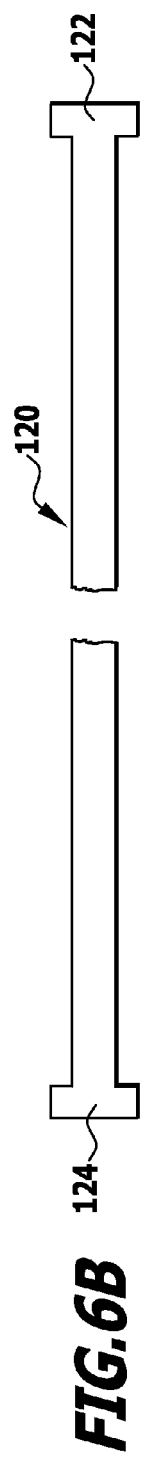

FIG. 6B shows an alternative longitudinal element 120 whose proximal and distal ends 122, 124 are each configured in a T-shape.

These proximal and distal ends configured in a T-shape can be placed in correspondingly configured receptacles on the inner shaft 106 or a separate annular collar, thus establishing fixation of the longitudinal elements 120 relative to and spaced apart from one another in a circumferential direction, while additionally offering a connection via which the forces are capable of being transferred from the proximal end to the distal end of the control apparatus 100.

Figure 6C:

A further variant is depicted in FIG. 6C, this variant providing a longitudinal element 130 having waisted proximal and distal end portions 132 and 134 respectively. These waisted ends 132 and 134 are capable of being fixed with somewhat less space requirement in a form-locking and/or a force-locking manner to the proximal and distal ends of an inner shaft 106 or to a separate annular collar.

Figure 6D:
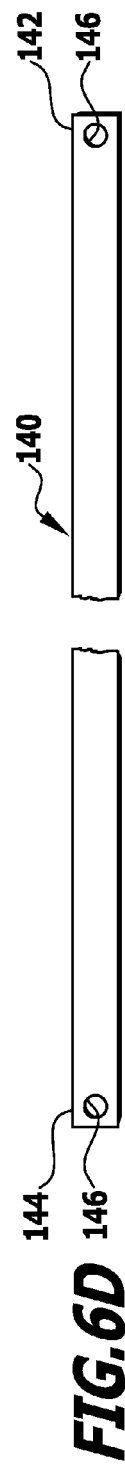

FIG. 6D shows a longitudinal element 140 which, similar to the longitudinal element 104, has a through-opening 146 at the proximal and distal ends 142, 144 thereof which can receive a projection provided on the inner shaft 106 or on a separate annular collar.

Figure 6E:
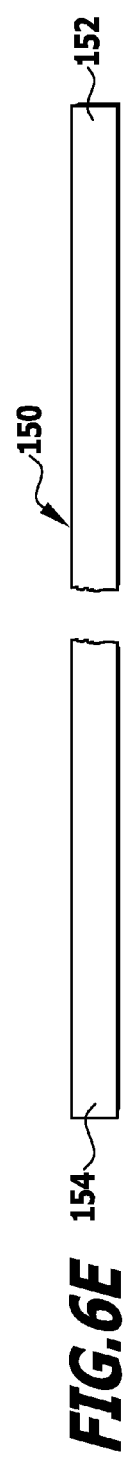

Finally, shown in FIG. 6E is the simplest version of the separate longitudinal elements in the form of a longitudinal element 150 which is capable of being fixed at its proximal and distal ends 152, 154 to an annular collar and optionally to a proximal and distal end of an inner shaft 106 by a substance-to-substance bond produced for example by adhesive bonding or welding.

Conceivably, a substance-to-substance bond to an annular collar or the inner shaft could alternatively also be used with the longitudinal elements 104, 120, 130, 140 in FIGS. 6A to 6D.

FIG. 7 gives an overview of different sheet materials which, formed into a tube, form a control element as it is used in the context of the control apparatus 12 constructed in accordance with the embodiment of FIGS. 1 to 4.

Figure 7A:
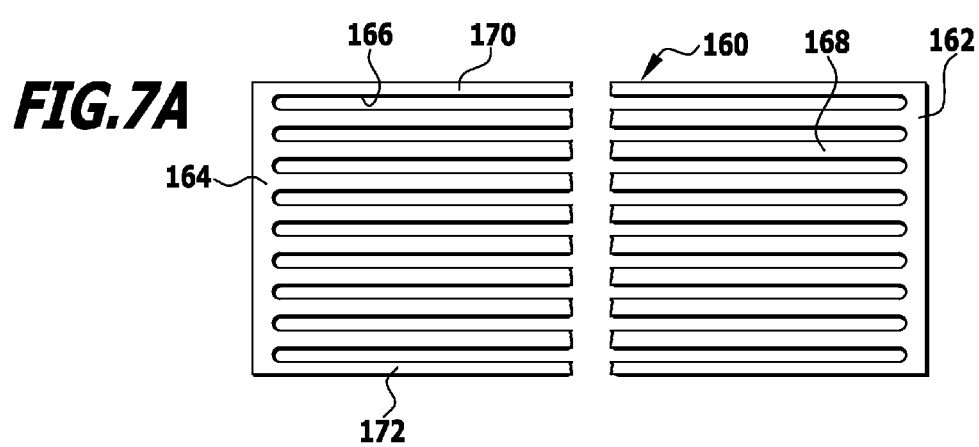
FIGS. 7A to 7C illustrate various alternative embodiments of longitudinal elements for forming a control element of a control apparatus constructed in accordance with the invention.

FIG. 7A shows a sheet material 160 having a proximal end 162 and a distal end 164.

Extending in the sheet material 160, between the proximal and distal ends 162, 164 thereof, are slots 166 which maintain the longitudinal elements 168 connected to the proximal ends and distal ends 162, 164 in spaced relation to one another, with the longitudinal elements 168 being integrally formed with the proximal and distal ends 162, 164.

The slots 166 are configured with their proximal and distal ends radiused with a radius corresponding to approximately half the width of the slots 166 between adjacent longitudinal elements 168.

When the sheet material 160 is formed into a tube, the laterally outer longitudinal elements 170 and 172 can lie in direct contact with each other and can also be connected together by a seam. In an embodiment thus configured, the width of the longitudinal elements 170, 172 will amount to approximately half the width of the longitudinal elements 168.

Alternatively, provision could be made for the laterally arranged longitudinal elements 170, 172 to be configured to have the same width as the longitudinal elements 168; in this case, the lateral longitudinal elements 170, 172, with the sheet material 160 rolled into a tube, are held at a distance corresponding to the width of the slot 166 in the sheet material 160.

In a further variant, one of the lateral longitudinal elements 170, 172 can be omitted, while the proximal and distal end portions 162, 164 have the same width as that in FIG. 7A. This then provides an area projecting over the last of the longitudinal elements in a transverse direction and this area can then be connected to the lateral end of the sheet material 160 by a seam.

While the sheet material 160 is rolled up into a control element in the form of tube and as such can be simply held between an inner and an outer shaft, thus fully satisfying its intended purpose of transferring forces from the proximal to the distal end of a control apparatus, a series of through-openings may be provided at the proximal and distal ends of the sheet material for additionally securing the control element in the assembled control apparatus, said through-openings being capable of receiving correspondingly configured projections provided on the inner shaft, similar to what has been described in connection with the embodiment of a control apparatus 12 in conjunction with FIGS. 1 to 4.

Figure 7B:
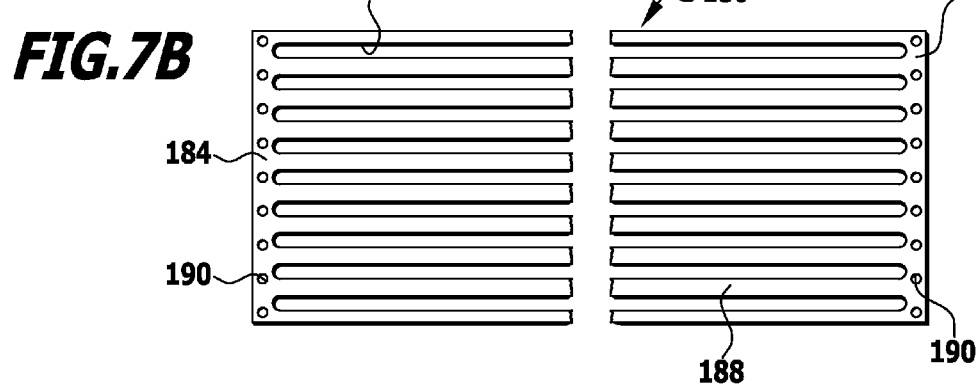

Such a development is shown in FIG. 7B in which a sheet material 180 has proximal and distal ends 182, 184 between which, again, longitudinal elements 188 maintained in spaced-apart relation by slots 186 extend analogously to the embodiment described in connection with FIG. 7A. However, additional through-openings 190 are provided in the area of the proximal and distal ends 182, 184.

Figure 7C:
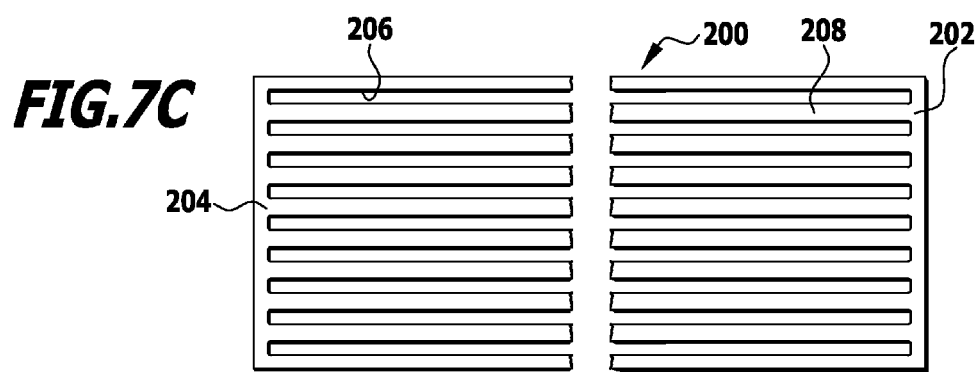

FIG. 7C shows a further alternative sheet material 200 having a proximal end 202 and a distal end 204 in which, again, slots 206 extend from the proximal end 202 to the distal end 204, fixing longitudinal elements 208 relative to and in spaced relationship to one another.

Here, unlike the embodiment of the sheet material 160 of FIG. 7A, the ends of the slots 206 are configured to be of rectangular shape.

Figure 8:
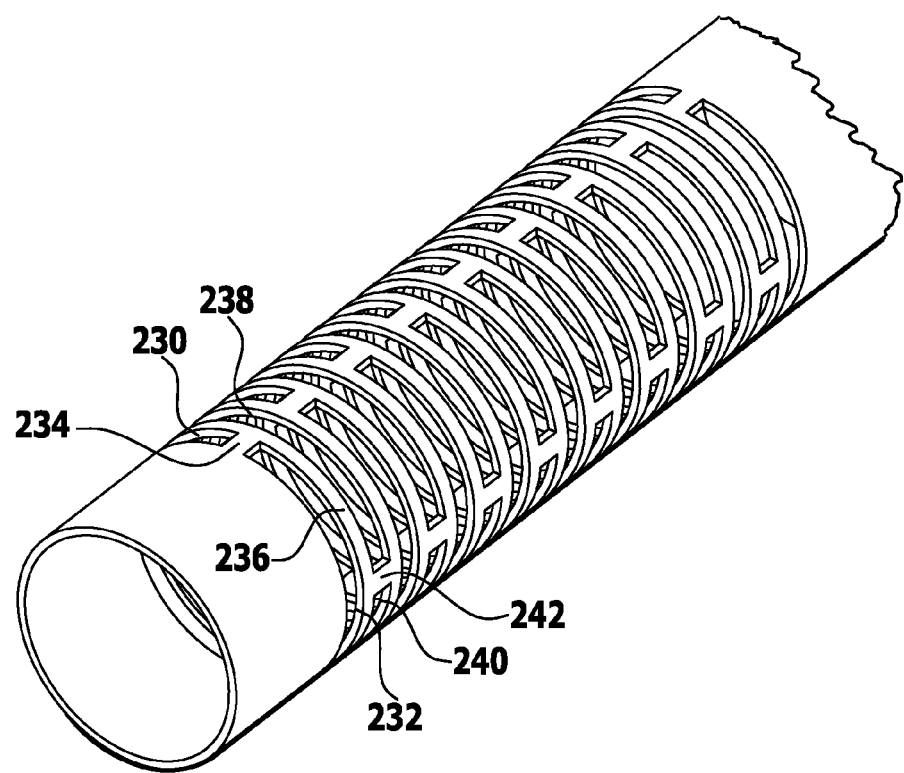
FIG. 8 depicts a variant of an articulation section of a shaft of a control apparatus constructed in accordance with the invention.

Finally, FIG. 8 shows yet another alternative embodiment of an articulation section for an inner and/or an outer shaft in which the articulating function is established by having slots extending in a circumferential direction arranged in offset relation with respect to one another.

In the case of the exemplary embodiment of FIG. 8, two slots 230, 232 are provided in a circumferential direction in each case, separated from each other only by a narrow web 234. In an axial direction, at a short distance 236, follows another pair of slots 238, 240 extending in a circumferential direction and separated from each other by a narrow web 242. The slots 230, 232 and 238, 240 are arranged in pairs with a 90° offset in a circumferential direction in each case so that the articulation zone allows movements in all directions with approximately the same expenditure of force.

The pattern of the alternatingly arranged slots 230, 232 and 238, 240 continues over the whole articulation zone of the shaft and with a material such as Nitinol allows for a very simple one-piece articulating structure to be configured.

The invention claimed is:

1. A control apparatus for use in endoscopes, comprising:
a proximal end section and a distal end section of the control apparatus, each of which comprises an articulation zone, and a central section arranged therebetween,
an outer hollow-cylindrical shaft,
an inner hollow-cylindrical shaft, and
a control element which is arranged between said inner and outer shafts and which has two or more force-transmitting longitudinal elements extending substantially from the proximal end section to the distal end section of the control apparatus for mechanically coupling the movement of the distal end section with the movement of the proximal end section,
wherein:
the longitudinal elements are arranged in spaced-apart relation to one another at substantially regular angular distances $b_{1, 2} \ldots b_n$ in a circumferential direction of the control apparatus and are fixed relative to one another in an area of proximal and distal end sections of the longitudinal elements in each case in the circumferential direction,
the angular distances $b_{1, 2} \ldots b_n$ of the longitudinal elements relative to one another, as measured in the circumferential direction, are selected such that the force-transmitting longitudinal elements are guided at least one of without contact in the circumferential direction and are guided in contact with at least one of the outer shaft and the inner shaft in a radial direction.

2. The control apparatus in accordance with claim 1, wherein the longitudinal elements are in contact with and guided by the outer and the inner shaft in a radial direction.

3. The control apparatus in accordance with claim 1, wherein a cross-section of the longitudinal elements is one of configured substantially in a shape of a circular arc segment or configured substantially in a shape of a rectangle.

4. The control apparatus in accordance with claim 1, wherein the control element with its longitudinal elements is formed by one of a longitudinally slotted tube, a longitudinally slotted sheet material that is formed into a tube, or individual rod-shaped elements which are fixed relative to one another at proximal and distal ends of the rod-shaped elements in the circumferential direction.

5. The control apparatus in accordance with claim 1, wherein an outside diameter of the outer shaft is selected to be in a range of approximately 1 mm to approximately 20 mm and an inside diameter of the inner shaft is selected to be in a range of approximately 0.05 mm to approximately 5 mm.

6. The control apparatus in accordance with claim 1, wherein the distal end sections of the longitudinal elements are fixed in the circumferential direction in angular positions that are different from angular positions in which are fixed the proximal end sections of the longitudinal elements associated with them in each case.

7. The control apparatus in accordance with claim 6, wherein the angular positions in which the distal end sections of the longitudinal elements are fixed in the circumferential direction differ by approximately 45° to 315°.

8. The control apparatus in accordance with claim 1, wherein the force-transmitting longitudinal elements are arranged in a shape of a helix between the shafts over at least part of a length of the longitudinal elements.

9. The control apparatus in accordance with claim 8, wherein the force-transmitting longitudinal elements are arranged substantially parallel to a longitudinal direction of the control apparatus in an area of at least one of the proximal and the distal end sections of the control apparatus and are arranged in a form of a helix in an area located therebetween.

10. The control apparatus in accordance with claim 8, wherein the force-transmitting longitudinal elements have one or more sections in the area between the proximal and distal end sections of the longitudinal elements which are arranged parallel to a longitudinal direction of the control apparatus.

11. The control apparatus in accordance with claim 1, wherein:
    articulation sections of at least one of the inner and the outer shaft comprise a plurality of separate annular segments, each of which has a first and a second end region in an axial direction,
    the first end region comprises two or more projections projecting in an axial direction and the second end region comprises two or more recesses for receiving said projections,
    the projections and recesses are arranged at regular distances in the circumferential direction on the respective annular segment,
    the annular segments are in articulating engagement with one another via the projections and recesses, and
    the annular segments are connected together in a form-locking manner via the projections and recesses in at least one of the axial direction and a radial direction.

12. The control apparatus in accordance with claim 11, wherein:
    the projections have, in the circumferential direction, a greater extension on a radially outer side than on a radially inner side, and
    the recesses have, in the circumferential direction, an extension at the radially inner side that is smaller than a corresponding extension of the projection on the radially outer side.

13. The control apparatus in accordance with claim 11, wherein:
    the projections each have, in the circumferential direction, a greater extension at a free end of the projection facing away from the annular segment than adjacent to the annular segment, and
    the recesses each have, in the circumferential direction, an extension at an open end of the recess that is smaller than the extension of the projection engaging in the recess at the free end thereof.

14. The control apparatus in accordance with claim 11, wherein the projections and recesses are configured to have an essentially trapezoidal shape in cross-section in at least one of the circumferential direction and the radial direction.

15. The control apparatus in accordance with claim 1, wherein the articulation zone of at least one of the outer shaft and the inner shaft comprise a wall section in which are arranged a plurality of slots spaced apart from one another and extending in the circumferential direction.

16. The control apparatus in accordance with claim 15, wherein the wall section of the inner shaft comprises two or more slots which extend completely through the cylindrical wall of the shaft and are arranged one behind the other in the circumferential direction.

17. The control apparatus in accordance with claim 16, wherein the wall section of the inner shaft comprises three or more slots arranged one behind the other in the circumferential direction.

18. The control apparatus in accordance with claim 15, wherein the wall section of the inner shaft comprises three or more slots which are, in an axial direction, arranged side by side.

19. The control apparatus in accordance with claim 1, wherein at least one of the articulation zones is configured to be elastic.

20. The control apparatus in accordance with claim 1, wherein the longitudinal elements of the control element are made of a steel alloy or Nitinol.

21. The control apparatus in accordance with claim 1, wherein at least one of the outer shaft and the inner shaft has a flexurally rigid section arranged between the proximal and distal articulation zones.

22. The control apparatus in accordance with claim 1, wherein the control element with its longitudinal elements is formed by individual rod-shaped elements which are fixed relative to one another at proximal and distal ends of the rod-shaped elements in the circumferential direction by use of an annular collar.

23. The control apparatus in accordance with claim 6, wherein the angular positions differ in the circumferential direction by approximately 10° to 350°.

24. The control apparatus in accordance with claim 15, wherein the slots extend completely through the wall of the shaft.

25. The control apparatus in accordance with claim 15, wherein the wall section of the inner shaft comprises three or more slots which are, in an axial direction, arranged side by side and offset relative to one another.

* * * * *